(12) United States Patent
Dittmer et al.

(10) Patent No.: US 7,767,210 B2
(45) Date of Patent: Aug. 3, 2010

(54) RNA VIRUS VACCINES AND METHODS

(75) Inventors: Dirk P. Dittmer, Chapel Hill, NC (US); Robert A. Floyd, Oklahoma City, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 173 days.

(21) Appl. No.: 11/639,023

(22) Filed: Dec. 14, 2006

(65) Prior Publication Data

US 2007/0292453 A1  Dec. 20, 2007

Related U.S. Application Data

(60) Provisional application No. 60/750,859, filed on Dec. 14, 2005.

(51) Int. Cl.
*A61K 39/12* (2006.01)
*C12N 7/06* (2006.01)

(52) U.S. Cl. ..................... 424/218.1; 435/238

(58) Field of Classification Search ........................ None
See application file for complete search history.

(56) References Cited

U.S. PATENT DOCUMENTS

| | | | |
|---|---|---|---|
| 3,456,053 | A | 7/1969 | Crawford |
| 4,950,665 | A | 8/1990 | Floyd |
| 6,346,529 | B1 | 2/2002 | Floyd et al. |
| 6,348,309 | B1 | 2/2002 | Mohr et al. |
| 2003/0091595 | A1 | 5/2003 | Chu |
| 2003/0104008 | A1 | 6/2003 | Loosmore et al. |
| 2003/0124511 | A1 | 7/2003 | Tauer et al. |
| 2003/0148261 | A1 | 8/2003 | Fikrig et al. |
| 2004/0018997 | A1 | 1/2004 | Reddy et al. |
| 2005/0053923 | A1 | 3/2005 | Beall et al. |

FOREIGN PATENT DOCUMENTS

| | | |
|---|---|---|
| EP | 06849958 | 2/2009 |
| WO | WO 00/34446 | 6/2000 |
| WO | PCT/US2006/047696 | 2/2008 |

OTHER PUBLICATIONS

Lanciotti, "Rapid Detection of West Nile Virus from Human Clinical Specimens, Field-collected Mosquitoes, and Avian Samples by a TaqMan Reverse Transcriptase-PCR Assay", Journal of Clinical Microbiology, Nov. 2000, p. 4066-4071, vol. 38, No. 11.
Floyd, et al., "Methylene blue photoinactivation of RNA viruses", *Antiviral Research*, (Mar. 2004) vol. 61, No. 3, pp. 141-151.
Myamae, "Functional Differences of Dyes in Inducing Respiratory Immunogenicity by Azo-, Thiazole-, Quinoline-, Re-active-, and Naphthol-Dye-Inactivated Sendai Viruses", *Microbiology and Immunology*, (1993) vol. 37, No. 3, pp. 213-220.
Papin et al., "Methylene blue photoinactivation abolishes West Nile virus infectivity in vivo", *Antiviral Research*, (Nov. 2005) vol. 68, No. 2, pp. 84-87.
Teschner, et al., "Photoinactivation of the Encephalomyocarditis Virus Brief Report", *Archives of Virology*, (1978) vol. 58, No. 3, pp. 249-252.

*Primary Examiner*—Stacy B Chen
(74) *Attorney, Agent, or Firm*—Dunlap Codding, P.C.

(57) ABSTRACT

The invention is a vaccine, and method of vaccination, against RNA viruses, including RNA viruses in the family Flaviviridae, which includes for example West Nile Virus, Yellow fever virus, Dengue fever virus, Hepatitis C virus, Pestiviruses, Bovine viral diarrhea virus, and Classical Swine fever virus, wherein the vaccine comprises the RNA virus or immunogenic portions thereof, which have been treated with and rendered non-pathogenic by a phenothiazine dye and visible light. The invention includes novel strains of WNV for use in producing a vaccine.

6 Claims, 8 Drawing Sheets

Fig. 3A anti-WNV IgM

Fig. 3B anti-WNV IgG

**Independent Repeat Exp.(7/19/2004):
MB/WNV protection
Challenge: 10^3 pfu WNV**

Fig. 8

RNA VIRUS VACCINES AND METHODS

CROSS-REFERENCE TO RELATED APPLICATIONS

The present application claims the benefit under 35 U.S.C. 119(e) of U.S. Provisional Application Ser. No. 60/750,859, filed Dec. 14, 2005. The entirety of which is hereby expressly incorporated herein by reference.

STATEMENT REGARDING FEDERALLY SPONSORED RESEARCH OR DEVELOPMENT

Not Applicable.

BACKGROUND

The unstable nature of the RNA molecule enables RNA viruses to evolve far more rapidly than DNA viruses, frequently changing their surface structures. RNA viruses in general have very high mutation rates as they lack polymerases which can find and fix mistakes, and are therefore unable to conduct repair of damaged genetic material. DNA viruses have considerably lower mutation rates due to the proofreading ability of DNA polymerases within the host cell. These mutations of RNA viruses make it more difficult for an organism to develop any kind of lasting immunity to the virus. Because each surviving virus can reproduce itself hundreds or thousands of times, mutations in the RNA sequence occur frequently. It has been estimated that a typical RNA virus may experience alterations of between 0.03 and 2 percent of its entire genome each year thus evolving faster than any other living organism. Mutations occur randomly across the entire length of the viral RNA, and so of course most are not beneficial, producing viruses which lack a needed protein or are otherwise disadvantaged. However, because of the enormous number of offspring produced by each virus, even a high rate of mutation does not threaten the survival of the virus, and when advantageous mutations do occur, they are rapidly selected for and reproduced. This evolution is known as antigenic drift. Thus at least one reason for the lack of suitable vaccines against most RNA viruses is the high rate of mutability of RNA viruses.

The West Nile Virus (WNV) of the Flaviviridae is such an RNA virus for which a vaccine is not available. WNV was first identified in 1937 in Africa and first found in North America in 1999. Migratory birds are considered the primary means whereby infection is spread within and between countries. The virus is transmitted by mosquitoes that have acquired infection by feeding on viremic birds. The virus is then amplified during periods of adult mosquito blood-feeding. Infected mosquitoes then transmit the virus to humans and animals upon feeding thereon.

WNV belongs to the Flaviviradae, a family of over 70 related viruses. WNV is an enveloped single-stranded positive sense RNA virus with a genome of approximately 11 kb encoding for three structural genes and seven non-structural genes.

West Nile Virus is the causative agent for West Nile Virus disease, particularly West Nile encephalitis, predominately in humans, other mammals and birds. The chief concern in both the United States and foreign countries is the lack of effective treatment for West Nile Virus disease. Anti-inflammatory drugs are used to combat swelling of central nervous system tissues, but beyond that no medical intervention is currently available.

The West Nile fever virus also affects horses, particularly in North America and Europe. These horses reveal signs of ataxia, weakness of the rear limbs, paresis evolving towards tetraplegia and death. Horses and camels are the main animals manifesting clinical signs in the form of encephalitis.

The virions of the West Nile fever virus are spherical particles with a diameter of 50 nm constituted by a lipoproteic envelope surrounding an icosahedric nucleocapsid containing a positive polarity, single-strand RNA. A single open reading frame (ORF) encodes all the viral proteins in the form of a polyprotein. The cleaving and maturation of this polyprotein leads to the production of several different viral proteins. The structural proteins are encoded by the 5' part of the genome and correspond to the nucleocapsid designated C (14 kDa), the envelop glycoprotein designated E (50 kDa), the pre-membrane protein designated prM (23 kDa), and the membrane protein designated M (7 kDa). The non-structural proteins are encoded by the 3' part of the genome and correspond to the proteins NS1 (40 kDa), NS2A (19 kDa), NS2B (14 kDa), NS3 (74 kDa), NS4A (15 kDa), NS4B (29 kDa), and NS5 (97 kDa).

Recent reports show that WNV can also be passed from human to human by blood transfusion. With the recent epidemic increase in WNV prevalence in the U.S. (CDC, 1999, 2002; Enserink, 2002; Lanciotti et al, 1999), a rise in WNV positive blood donors and rising need for methods to inactivate WNV in blood products can be expected.

Potential vaccines for WNV are described, for example, in U.S. Patent Publication Nos. 2003/0148261A1, 2003/0104008A1 and 2003/0091595A1. Publication No. 2003/0091595A1 describes a WNV vaccine that includes an inactivated whole or subunit WNV. Publication No. 2003/0104008A1 discloses a vector, such as recombinant avipox virus, containing and expressing exogenous polynucleotide(s) from WNV to induce an immune response against WNV. These recombinant WNV vaccines include a vector containing a polynucleotide having a single encoding frame corresponding to, for example, prM-E, M-E and prM-M-E. The vector may include several separate polynucleotides encoding the different proteins (e.g., prM and/or M and E). The vector can also include polynucleotides corresponding to more than one WN virus strain, for example, two or more polynucleotides encoding E or prM-M-E of different strains. Furthermore, the vector can include one or more nucleotide sequences encoding immunogens of other pathogenic agents and/or cytokins. Publication No. 2003/0148261A1 describes various WNV polypeptides and immunogenic fragments for use in WNV vaccines. These vaccines are produced recombinantly using various vectors encoding WNV polypeptides and the vectors are expressed by a variety of host cells.

Methylene Blue (3,7-Bis(dimethylamino)phenothiazin-5-ium chloride), also referred to herein as MB, is FDA approved for oral administration and has been reported to be effective as an antiseptic, disinfectant, and antidote for cyanide and nitrate poisoning. The drug MB has seen limited use to inactivate HIV in blood products (Lambrecht et al, 1991; Mohr et al, 2004).

Further it is known that MB and other phenothiazine dyes (e.g., neutral red, thionine, and toluidine blue) can, in combination with wavelengths of visible light (e.g., 660 nm) inactivate certain viruses (e.g., U.S. Pat. Nos. 6,348,309 and 6,346,529).

BRIEF DESCRIPTION OF THE DRAWINGS

Figures 3A, 3B:
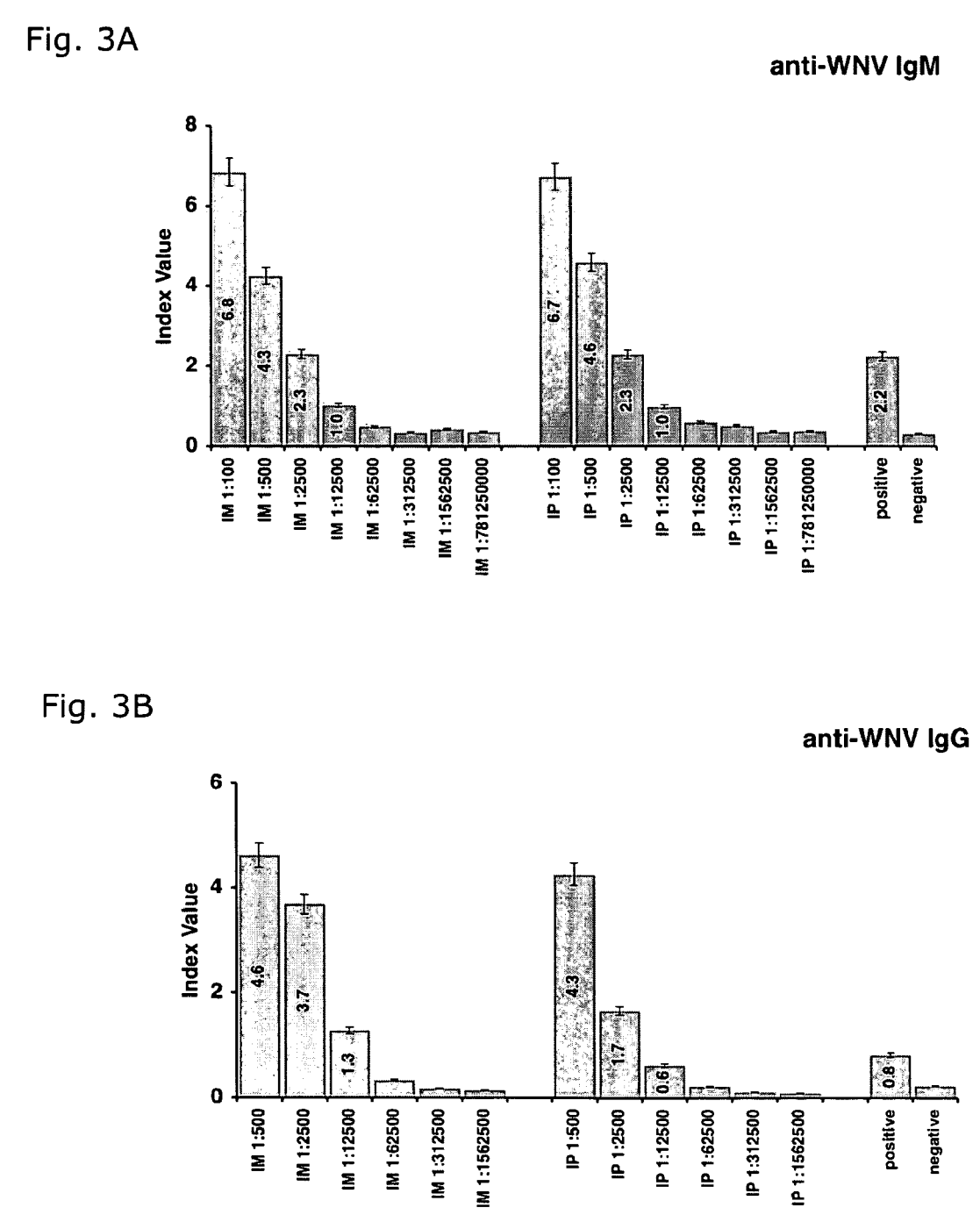

FIG. 3 shows that MB-inactivated virus does not cause disease in mice.

FIG. 8: Effects of intra muscular (IM) or intra peritoneal (IP) immunization with MB-inactivated WNV on mouse survival after challenge with WNV (dosage $10^3$ pfu).

DESCRIPTION OF THE INVENTION

Figure 1:
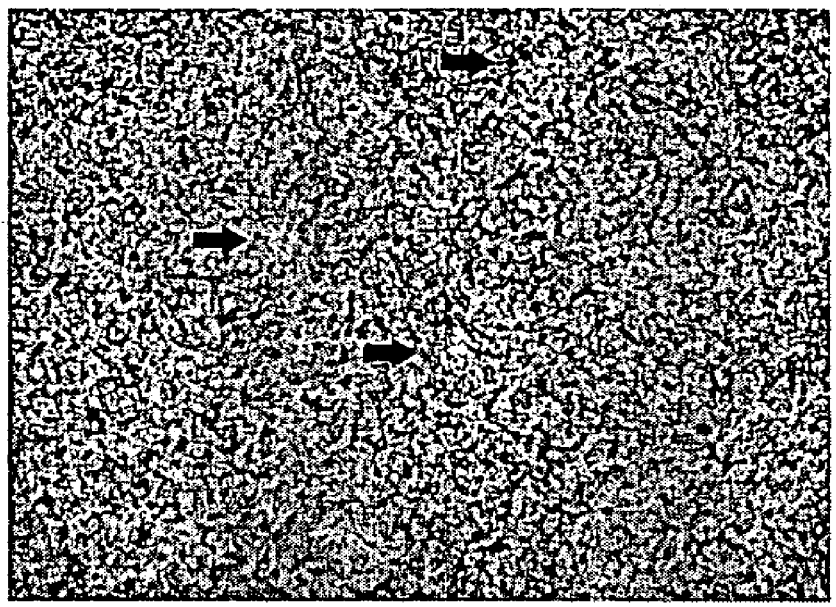
FIG. 1 shows images of a plaque assay for OK02 and OK03 isolates of WNV on Vero cells at 4× magnification (A) or 40× magnification (B).
Figure 1:
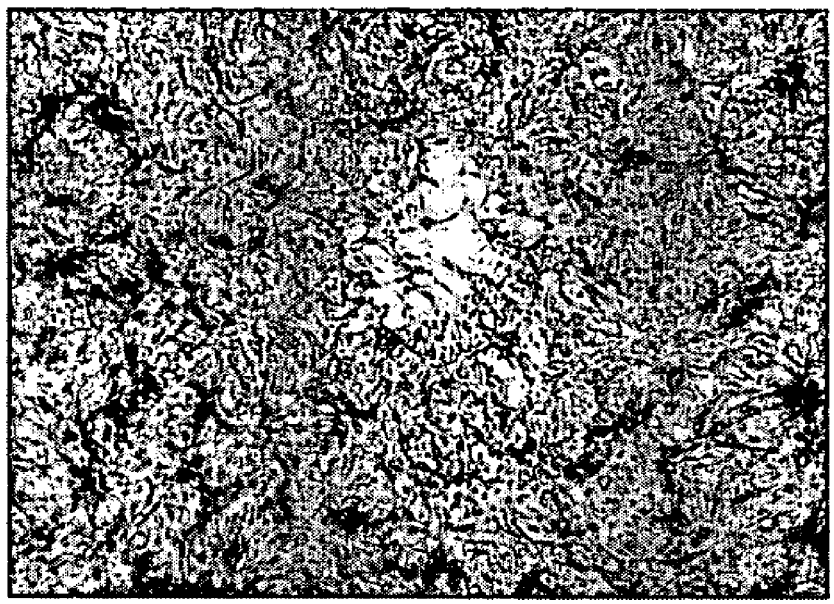

The present invention in one embodiment is directed to a vaccine against RNA viruses, particularly those in the family Flaviviridae, which includes for example West Nile Virus, Yellow fever virus, Dengue fever virus, Hepatitis C virus, Pestiviruses, Bovine viral diarrhea virus, and Classical Swine fever virus (and others as described elsewhere herein). The vaccine comprises at least one virus, or one or more immunogenic portions thereof, which have been treated with and rendered non-pathogenic by a phenothiazine dye and visible light. More particularly, the RNA virus or immunogenic portion thereof may have been rendered non-pathogenic by phenothiazine dyes, including, but not limited to, Methylene Blue (MB), Methylene Green, 1-methyl MB, 1,9-dimethyl MB, Azure A, Azure B, Azure C, thionine, and toluidine blue, or by squalene. More broadly, the invention comprises a vaccine or composition comprising an RNA virus or immunogenic portions thereof which have been rendered non-pathogenic by chemicals which induce RNA:RNA or RNA:protein crosslinking.

Further, the invention contemplates vaccines produced via the above inactivation techniques which are directed against any RNA virus including, but not limited to influenza, HIV and National Institute of Allergy and Infectious Diseases (NIAID) Category A, B and C priority pathogenic viruses and other RNA viruses described elsewhere herein.

Animal RNA viruses can be placed into about four different groups depending on their mode of replication, including:

(1) Positive-sense viruses which have their genome directly utilized as if it were mRNA, producing a single protein which is modified by host and viral proteins to form the various proteins needed for replication. One of these includes RNA replicase, which copies the viral RNA to form a double-stranded replicative form which in turn directs the formation of new virions;

(2) Negative-sense viruses which must have their genome copied by a RNA polymerase or transcriptase to form positive-sense RNA. This positive-sense RNA molecule acts as viral mRNA, which is translated into proteins by the host ribosomes. The resultant protein goes on to direct the synthesis of new virions, such as capsid proteins and RNA replicase, which is used to produce new negative-sense RNA molecules;

(3) Double-stranded reoviruses which contain up to a dozen different RNA molecules which each code for a mRNA. These all associate with proteins to form a single large complex which is replicated using virally-encoded replicase to form new virions; and (4) Retroviruses which are single-stranded but unlike other single-stranded RNA viruses they use DNA intermediates to replicate. Reverse transcriptase, a viral enzyme that comes form the virus itself after it is uncoated, converts the viral RNA into a complementary strand of DNA, which is copied to produce a double stranded molecule of viral DNA which goes on to direct the formation of new virions.

Because of the high rates of mutability of RNA viruses as noted above, it would be desirable to have a method such as that described herein for quickly manufacturing new or modified vaccines based on newly evolving strains of RNA viruses.

RNA viruses which could be treated and modified as described herein for manufacturing novel vaccines include, but are not limited to, those in the following RNA virus families:

Arenaviridae, such as lymphcytic choriomeningitis virus (LCM), Lassa virus, Junin, Tacaribe, Pichinde viruses, Machupo virus, and Guanito virus;

Bornaviridae, such as Borna disease virus;

Bunyaviradae, such as Hanta virus, California encephalitis virus, Japanese encephalitis virus, LaCrosse virus, Rift Valley fever virus, Bunyavirus, Arbovirus, Nairobi sheep disease virus, Phlebovirus, and Tospoviruses;

Caliciviridae, such as Human and animal caliciviruses;

Coronaviridae, such as SARS Coronavirus;

Filoviridae, such as Ebola virus and Marburg virus;

Flaviviridae, such as Yellow Fever virus, Dengue Fever virus, West Nile virus, Hepatitis C virus, Pestiviruses, Bovine Viral Diarrhea virus, and Classical Swine Fever virus (and others as indicated below);

Nodaviridae, such as Nodaviruses;

Orthomyxoviridae, such as Influenza virus type A, Influenza virus type B, Influenza virus type C, Thogotovirus, and Fowl Plague disease virus;

Paramyxoviridae, such as Parainfluenza viruses, Mumps virus, Measles virus, Subacute sclerosing panencephalitis (SSPE) virus, Respiratory syncytial virus (RSV), Pneumoviruses, "TPMV-like viruses", Newcastle Disease virus, Rinderpest virus, and Canine Distemper virus;

Picornaviridae, such as Human Enteroviruses, including Poliovirus, Coxsackie virus A, Coxsackie virus B, Hepatitis A virus, and Rhinoviruses, Foot and Mouth Disease virus, Enterovirus 70, Apthoviruses, and Cardioviruses;

Reoviridae, such as Colorado Tick fever virus, Rotaviruses, Reoviruses, Coltivirus and Orbiviruses;

Retroviridae, such as Human immunodefficiency virus (HIV), Human T-lymphotrophic virus (HTLV), Feline Leukemia virus (FeLV), Friend Leukemia virus (FLV), and MMTV (Mouse Mammary Tumor virus);

Rhabdoviridae, such as Rabies virus, and Vesicular Stomatitis virus; and

Togaviridae, such as Eastern Equine Encephalitis virus, Western Equine Encephalitis virus, Rubella virus (measles), Alphaviruses, and Ross River virus.

More particularly, viruses in the Flaviviridae for which vaccines can be produced using the methods of the present invention include, for example, those in the genera Flavivirus and Pestivirus, the "Hepatitis C-like viruses", and those in the Yellow fever virus group, Tick-borne encephalitis virus group, Rio Bravo group, Japanese encephalitis group, Tyuleniy group, Ntaya group, Uganda S group, Dengue group, and Modoc group. More specifically, the viruses of the Flaviviridae which may be used in the present invention include, for example, but are not limited to, Gadgets Gully virus, Kyasanur Forest disease virus, Langat virus, including the British, Irish, Louping ill, Spanish and Turkish subtypes, Omsk hemorrhagic fever virus, Powassan virus, Karshi virus, Royal Farm virus, Tick-borne encephalitis virus, including the European, Far Eastern, and Siberian subtypes, Kadam virus, Meaban virus, Saumarez Reef virus, Tyuleniy virus, Aroa virus, Bussuquara virus, Iguape virus, Naranjal virus, Dengue virus 1, Dengue virus 2, Dengue virus 3, Dengue virus 4, Kedougou virus, Cacipacore virus, Japanese encephalitis virus, Koutango virus, Alfuy virus, Murray Valley encephalitis virus, St. Louis encephalitis virus, Usutu virus, Kunjin virus, West Nile virus, Yaounde virus, Kokobera virus, Stratford virus, Bagaza virus, Ilheus virus, Rocio virus, Israel turkey meningoencephalomyelitis virus, Ntaya virus, Tembusu virus, Spondweni virus, Zika virus, Banzi virus, Bouboui virus, Edge Hill virus, Jugra virus, Potiskum virus, Saboya virus, Sepik virus, Uganda S virus, Wesselsbron virus, Yellow fever virus, Entebbe bat virus, Sokoluk virus, Yokose virus, Apoi virus, Cowbone Ridge virus, Jutiapa virus, Modoc virus, Sal Vieja virus, San Perlita virus, Bukalasa bat virus, Carey Island virus, Dakar bat virus, Montana myotis leukoencephalitis virus, Batu Cave virus, Phnom Penh bat virus, Rio Bravo virus, Cell fusing agent virus, Tamana bat virus, Border disease virus-BD31, Border disease virus-X818, Bovine viral diarrhea virus 1-CP7, Bovine viral diarrhea virus 1-NADL, Bovine viral diarrhea virus 1-Osloss, Bovine viral diarrhea virus 1-SD1, Bovine viral diarrhea virus 2-C413, Bovine viral diarrhea virus 2-New York'93, Bovine viral diarrhea virus 2-strain 890, Classical swine fever virus-Alfort/187, Classical swine fever virus-Alfort-Tübingen, Classical swine fever virus-Brescia, Classical swine fever virus-C, Pestivirus of giraffe, Hepatitis C virus, including genotype 10, genotype 11, genotype 1a, genotype 1b, genotype 2a, genotype 2b, genotype 3a, genotype 4a, genotype 5a, genotype 6a, and GB virus B, GB virus A, GB virus C, and Hepatitis G virus-1.

Flavivirid viruses particularly contemplated for use herein include, Dengue virus, Yellow fever virus, St. Louis encephalitis virus, Japanese encephalitis virus, Murray Valley encephalitis virus, West Nile virus, Rocio virus, Tick-borne encephalitis virus, Omsk hemorrhagic fever virus, Kyasunur Forest disease virus, Powassan virus, Pestiviruses, and Hepatitis C virus.

Other RNA viruses contemplated herein which can be treated to produce a vaccine as contemplated herein include, but are not limited to, Astroviruses, Norwalk-like viruses, Hepatitis D and E viruses, Nipah virus, LR1 virus and Benyviruses.

The present invention also contemplates novel strains of WNV (OK03, OK02) for use in producing a vaccine.

The present invention also contemplates novel primers and their use in recognizing and amplifying all of or portions of the WNV genome for diagnosing WNV infections, for quality control of the vaccine, or for identifying the presence of WNV in blood or blood products.

Currently there exists no FDA-approved vaccine against WNV for human use and there exist no FDA-approved vaccines against NIAID category A and category B priority viruses for human use. These agents have been identified by the US government (NIH) as most likely to be altered and abused as weapons for bioterrorism attacks. Hence, it is necessary to be able to detect these known agents and any novel derivatives, natural or engineered, and to speedily develop and deploy a vaccine against them. Chemical inactivation by MB is a more speedy means to develop a vaccine against abused, altered or emerging agents than genetically engineered life vaccines or recombinant protein-based formulations.

Strains OK02 and OK03 described herein are more recent isolates of WNV than available from prior research and are representative of the clade/type of WNV that is responsible for the current epidemic in the US. Strains OK02 and OK03 were deposited with the ATCC in the American Type Culture Collection (ATCC) located at 1081 University Boulevard, Monassas, Va., 20110-2209, USA, on Dec. 14, 2006, and have ATCC accession numbers PTO-8079 and PTA-8078, respectively.

Prior to the present invention, it was not known whether or not WNV is affected by treatment with MB with light. Herein it is shown that treatment of WNV with MB and light inactivates the virus and that the inactivated WNV (or other Flavivirids or other RNA viruses) can stimulate an antibody response.

The vaccines produced according to the processes described herein offer the following improvements over current vaccines: there is currently no vaccine against WNV or other Flavivirid viruses that is approved for human use. Further, there is currently no vaccine against NIAID category A or B priority pathogenic viruses that is approved for human use. Since the pathogenicity of the virus in these vaccines is completely inactivated, the vaccines of the present invention offer a superior safety profile over live-virus, attenuated vaccines. The chemically-inactivated vaccines contemplated herein can never revert to or be reengineered to wild-type/virulent virus, nor can the vaccine, once distributed be re-isolated and amplified for malicious purposes or for the purpose to infringe upon the original product.

Furthermore, chemically-inactivated vaccines are safe for use in immunocompromised patients (e.g., children, transplant recipients, AIDS patients, and individuals suffering from immunosuppressive conditions such as malaria, malnutrition and co-infection with other viruses or parasites). The preferred chemical described herein (MB), which is used for inactivation is without any side effects in humans and has been used in patients since the 1750's to investigate kidney function. Chemical inactivation allows (1) the production of seasonal vaccines with ease and no prior knowledge about the biology of the target, (2) the production of vaccines at low cost, and (3) the production of vaccines at rapid speed, such as is needed in the event of a bioterrorist attack. The inactivation of the RNA genome yields a superior vaccine relative to inactivation of protein e.g., by formalin as introduced by J. Salk. Protein crosslinking changes the structure of the outer viral glycoproteins, which are the target for neutralizing antibodies. Hence, many epitopes presented by a chemically cross-linked vaccine differ from epitopes presented by the live virus and hence lower vaccine efficacy. The mechanism described herein does not affect the outer glycoproteins and hence yields a superior target that is more similar to wild-type virus than a protein-crosslinked vaccine and is expectedly more potent.

While the RNA-crosslinking chemicals (e.g., MB, squalene) have been proposed herein for the inactivation of WNV, other Flavivirids, or other RNA viruses, herein they are not FDA approved or in active use for patients. The RNA-crosslinking chemical (e.g., MB, squalene) have been proposed for the inactivation of other viruses, but those disclosures do not cover further use of the inactivated viruses in a vaccine. Strains OK02 and OK03 are more recent isolates of WNV and representative of the lade of WNV that is responsible for the current epidemic in the US compared to, for example, strain NY99, which forms the basis of many prior or ongoing vaccine efforts.

The WNV primer set of the present invention is the only WNV primer set that can (1) amplify the complete WNV genome and yield pieces of a size suitable for rapid sequencing from mosquitoes, birds, other animals and humans, that can (2) be used for quantitative real-time PCR based quantification of virus for diagnosis, quality control of vaccines, as a tool for high-throughput drug screens and to yield products for strain typing and sequencing, and (3) that can be used simultaneously for the two different purposes set forth herein. Currently, at least two different primer sets are required to accomplish either.

Methods described below, though specific for WNV, can be applied to any of the RNA viruses described elsewhere herein, particularly those methods related to virus inactivation and vaccine production.

Methods

Specimens: (a) RNA was obtained from 56 WNV-positive mosquito pools (both *Aedes* and *Culex* species) stored at −80° C. from the 2002 and 2003 season. (b) Tissues (brain, kidney, heart) were obtained from 12 individual WNV-infected blue jays available for re-isolation of other WNV strains. (c) Two WNV strains (OK02, OK03) were isolated that grow in culture.

Clarified suspensions of tissue were prepared by placing the tissue samples into 5 ml snap top tubes (FALCON 352063) together with 2 ml of homogenization buffer (2×PBS with 0.05M Tris/HCl pH 7.6, 1% (w/v) bovine serum albumin, 4.2 mM sodium bicarbonate, 0.1 µg/ml streptomycin, and 1 µg/ml amphotericin B) and four copper clad steel beads (4.5 mm), then vortexed for 5 times 45 s. The homogenate was subsequently centrifuged in 2 ml tubes (Sarstedt, Germany) at 13,000 rpmi in an eppendorf centrifuge for 5 min to remove solids from the supernatant (SN).

WNV RNA isolation and cDNA synthesis: RNA was isolated as previously described (Fakhari, F. D., and D. P. Dittmer. 2002). cDNA was synthesized as per our published procedures (Dittmer, D. P. 2003; Papin et al., 2004). Briefly, 500 ng of RNA was reverse transcribed in a 20 µl reaction with 100 U of SUPERSCRIPTII reverse transcriptase (INVITROGEN INC., Carlsbad Calif.), 2 mM deoxyribonucleoside triphosphates, 2.5 mM $MgC_{l2}$, 1 U of Rnasin (all from APPLIED BIOSYSTEMS, Foster City, Calif.), and 0.5 µg of appropriate primers (see below). The reaction mix was sequentially incubated at 42° C. for 45 min, 52° C. for 30 min, and 70° C. for 10 min. The reverse transcription reaction was stopped by heating to 95° C. for 5 minutes. Net, 0.5 U RnaseH (INVITROGEN INC., Carlsbad, Calif.) was added, and the reaction incubated at 37° C. for an additional 30 min. Afterwards, the cDNA pool was diluted 25-fold with diethyl pyrocarbonate (DEPC)-treated, distilled $H_2O$ and stored at 80° C.

Real-time QPCR for viral load: cDNA is analyzed for WNV following our previously established procedures (Dittmer, D. P., 2003; Fakhari, F. D., and D. P. Dittmer, 2002) with the exception that we use the ABI HighFidelity polymerase mix (APPLIED BIOSYSTEMS, INC.) rather than Taq Polymerase which has a lower fidelity and may lead to sequence errors (Malet, et al., 2003). The final PCR reaction contains 2.5 µl of forward and reverse primer (final concentration 300 nM each), 7.5 µl of 2×PCR mix (2 U HighFidelity polymerase, nucleotides and Mg according to the manufactures recommendations), and 5 µl of cDNA. Real-time PCR are preformed using an ABI PRIZM5700 or ABI PRIZM7700 machine (APPLIED BIOSYSTEMS, Foster City, Calif.) and universal cycling conditions (2 min at 50° C., 10 min at 95° C., 40 cycles of 15 sec at 95° C., and 1 min at 60° C.). CT values are determined by automated threshold analysis.

Sequencing of PCR products: Real-time QPCR products were sequenced after subcloning into pCR2.1 (INVITROGEN INC.) according to the manufacturers procedures, and transformed into DH5alpha cells. Positive clones were identified by IPTG/X-gal screening and miniprep DNA prepared using the BIORAD miniprep kit (BIORAD INC.). Inserts were identified by EcoRI and XbaI/HindIII digest and positive clones were subjected to sequencing using M13forward and M13reverse primers, the primer binding sites for which are present in the pCR2.1 vector.

Sequence analysis: Sequences were determined by standard methods.

Mouse infection and pathology: Mice were housed in HEPA filtered BSL-3 certified cages (BIOZONE INC.). Groups of mice were injected with WNV strain OK02 or OK03. Mice were observed daily. Hind leg paralysis was determined by observation, and such mice were unable to walk if nudged gently. Paralyzed mice were euthanized by $CO_2$ generated from cylinders according to AAALAC regulations.

MB inactivation of West Nile Virus. 1 ml aliquots of WNV at a concentration of $10^7$ pfu were mixed with MB (SIGMA INC.) to achieve the desired final concentration of MB in the reaction mixture. Mixtures were incubated for 20 minutes in the dark at room temperature and then subsequently for 10 minutes at 10 cm distance from a 40 watt fluorescent white culture hood light at room temperature. Samples were then diluted to the desired concentration of WNV for plaque assay. Inactivated virus was prepared fresh for each assay and never kept for longer than 2 hours at 4° C. before use. It is contemplated that other RNA viruses as described herein can be similarly treated for vaccine formation.

Plaque Assays. Five-fold serial dilutions of WNV strains either mock-treated or treated with MB were placed onto Vero cell monolayers cultured in either 6-well plates or T25 culture flasks (GREINER INC.). Virus aliquots were allowed to attach to the cells for 1 hour at normal cell culture conditions. After one hour the virus was aspirated from the cells. The monolayers were washed twice with phosphate-buffer saline (PBS) and overlayed with 2 ml or 5 ml (6-well or T25, respectively) of 1% methylcellulose (SIGMA INC.) medium supplemented with 2% calf serum. Cells were incubated for 5 days. Afterwards the methylcellulose was removed, the monolayers were washed once with PBS and fixed with 100% ice-cold methanol for 5 minutes. The monolayers were subsequently stained with 0.5% Giemsa stain (SIGMA INC.) and plaques counted using a MZ12 dissecting microscope (LEICA INC., Germany).

Animal Studies. Normal BalbC/j mice ranging in age from 6-8 weeks were obtained from JACKSON LABORATORIES (Bar Harbor, Me.). Severely combined immunodeficient (SCID) mice also 6-8 weeks in age were purchased from TACONIC FARMS (Germantown, N.Y.). Mice were kept in groups of 5 animals per cage. We used filter-top cages inside a laminar flow hood/rack and a BSL-3 certified mouse cage unit (BIOZONE INC.). All manipulations of animals and the changing of cages were performed inside a biosafety cabinet following BSL-3 procedures. The mouse facilities were fully accredited by the American Association for Accreditation of Laboratory Animal Care (AAALAC). Studies were approved by the local institutional Animal Care and Use Committee (IACUC). Mice were infected with $10^4$ plaque-forming units (pfu) of mock-treated WNV or WNV treated with MB by i.p. injection in a total volume of 200 μl. Animals were monitored daily and sacrificed when signs of hindleg paralysis or loss of mobility became apparent.

Results (A) Isolation of WNV Strains OK02 and OK03 by Plaque Assay on Vero Cells.

We isolated and sequenced WNV from a 2002 Oklahoma isolate (OK02) and from a 2003 Oklahoma isolate (OK03) (see FIG. 1). The isolate was obtained from an infected blue jay and passaged twice on Vero cells. RNA was isolated, reverse-transcribed and PCT-amplified. The amplified product was sequenced directly using both primers. Direct comparison of overlapping sense and anti-sense sequences yielded 100% sequence identity for the PCR product (data not shown). A blastn comparison of OK02 and OK03 identified a number of nucleotide changes relative to strain NY-99 (including, but not limited to, those in Table 1). The complete sequence of NY99 (Genbank Accession No. AF 196835.2) is hereby expressly incorporated by reference herein in its entirety.

(B) Inactivation of WNV Strain OK02 and OK03 by Methylene Blue+Light.

Figure 2:
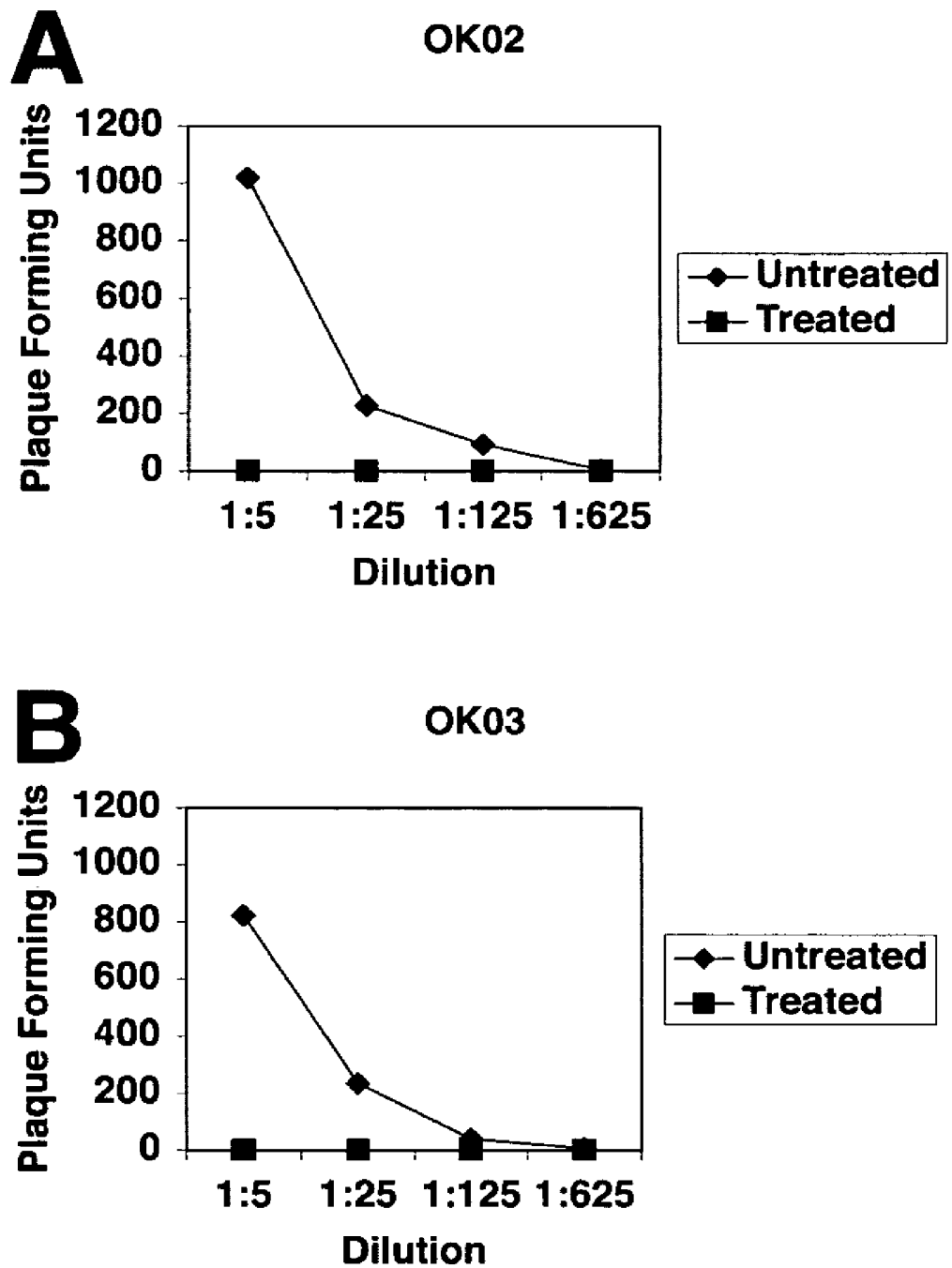
FIG. 2 shows how MB and light inactivates OK02 (A) and OK03 (B) in vitro.
Figure 4A:
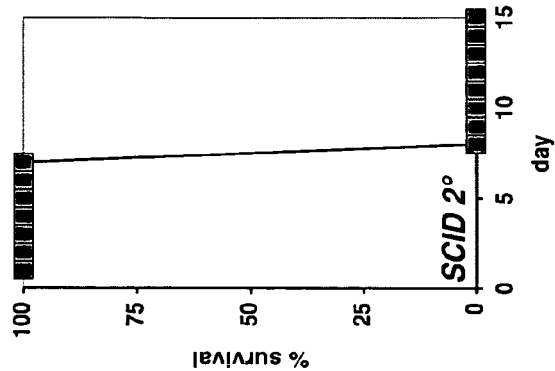
FIG. 4: Effects of active WNV (A and B) without prior immunization, after prior immunization of an immunocompetent mouse with MB-inactivated WNV (C), and after prior immunization with MB-inactivated WNV of an immunodeficient mouse (D) on mouse survival (dosage $10^4$ pfu).
Figure 4B:
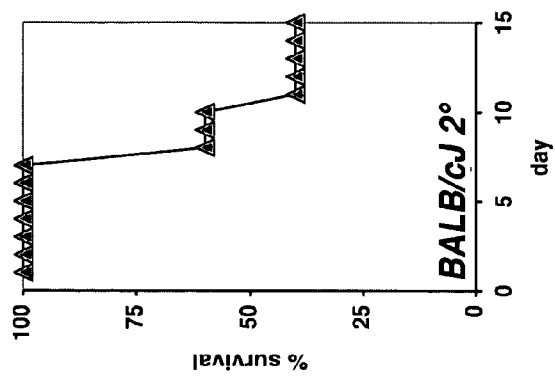
Figure 4C:
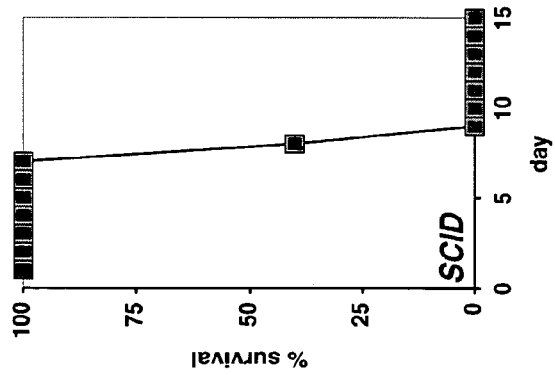
Figure 4D:
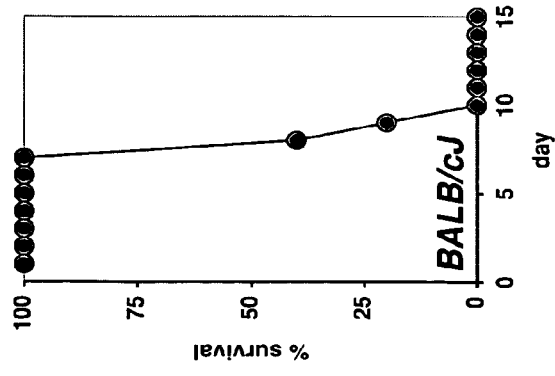

As a member of the Flaviviridae family of viruses, WNV utilizes a RNA dependent RNA polymerase for replication. This process is relatively error prone and can lead to the creation of multiple strains. To test the ability of MB to inactivate multiple WNV strains, MB was tested against multiple strains of WNV, including OK02, OK03 and NY-99 (the 1999 prototype virus NY-99 and the more recent Oklahoma isolates from 2002 and 2003). $5 \times 10^3$ pfu of OK03 WNV was incubated with 2 μM MB and light. The comparison of the inactivation of OK03 and OK02 is shown in FIG. 2. As observed, MB above 2 μM reduced the viral activity of the OK02 strain of WNV by $\geq 10^3$ (FIG. 2, panel A). This held true for the OK03 strain of WNV virus (FIG. 2, panel B) as well as for the NY-99 strain (data not shown). This demonstrates the efficacy of MB to photo-inactivate different strains of WNV. It is contemplated that other RNA viruses as described herein can be similarly treated for vaccine formation.

(C) Safety of the WNV Vaccine in Mice

OK02 WNV was tested for its ability to cause mortality and morbidity in mice. It was previously published that $\leq 10^4$ pfu

TABLE 1

Comparisons of OK02 and OK03 Genetic Sequences with Strain NY-99 of WNV.

| Sequenced | Size | No changes | Change | orf | aa | change |
|---|---|---|---|---|---|---|
| OK03 comparison to WNV NY-99 strain (AF196835.2) | | | | | | |
| 844-1230* | 387 | 0 | — — | M & ENV | — | — |
| 2628-3107* | 505 | 1 | 2832 t < c | NS1 | — | — |
| 2158-2647* | 490 | 2 | 2394 t < c | ENV | del | 717-728 |
| | | | 2466 c < t | ENV | del | 717-728 |
| 5571-6061* | 492 | 1 | 5804 ins < a | NS3 | del | 1903 |
| 1724-1914 | 191 | 3 | 1832 g < t | ENV | n/a | |
| | | | 1868 c < t | ENV | n/a | |
| | | | 1901 t < c | ENV | n/a | |
| 2222-2168 | 55 | 0 | — — | ENV | n/a | |
| 7809-8042 | 234 | 5 | 7820 g < del | NS5 | n/a | |
| | | | 7938 t < c | NS5 | n/a | |
| | | | 8001 t < c | NS5 | n/a | |
| | | | 8034 t < c | NS5 | n/a | |
| | | | 8026 g < t | NS5 | n/a | |
| 8312-8060 | 253 | 0 | — — | NS5 | n/a | |
| 5803-5715 | 89 | 0 | — — | NS3 | n/a | |
| 5303-5431 | 129 | 0 | — — | NS3 | n/a | |
| OK02 comparison to WNV NY-99 strain (AF196835.2) | | | | | | |
| 844-1229* | 386 | 0 | — — | M & ENV | — | — |
| 1724-2222* | 499 | 1 | 2121 g < a | ENV | — | — |
| 7809-8312* | 504 | 3 | 7938 t < c | NS5 | — | — |
| | | | 8189 a < g | NS5 | 2698 | D < G |
| | | | 8193 g < a | NS5 | 2699 | INS < W |
| 9604-10110* | 507 | 0 | — — | NS5 | — | — |
| 5803-5467 | 336 | 1 | 5455 t < c | NS3 | n/a | |
| 5303-5497 | 195 | 1 | 5416 a < g | NS3 | n/a | |
| 2628-2943 | 316 | 1 | 2924 g < t | NS1 | n/a | |
| 3131-2945 | 187 | 0 | — — | NS1 | n/a | |
| 4605-4859 | 255 | 2 | 4803 c < t | NS3 | n/a | |
| | | | 4845 t < c | NS3 | n/a | |
| 5112-4923 | 191 | 2 | 4960 t < c | NS3 | n/a | |
| | | | 4962 ins < c | NS3 | n/a | |
| 2152-2287 | 136 | 0 | — — | ENV | n/a | |
| 2647-2407 | 241 | 2 | 2466 g < a | ENV | n/a | |
| | | | 2446 g < a | ENV | n/a | |

*assembled pair (forward and reverse sequencing)

of WNV i.p. are lethal in BalbC/j mice with an average survival time of 9 days (Kramer, L., and K. Bernard. 2001). Using this study as a guideline we infected one group of BalbC/j mice (n=5) with a dose of $10^4$ pfu/animal of WNV strain OK02. By day nine only 40% of the mice were alive. By day 10 all mice (100%) had succumbed to infection, yielding a mean survival of time of 9.4 days consistent with previously published studies (FIG. 3, panel A, black dots). We then tested the ability of MB to block WNV strain OK02 lethal infection in mice. Reinforcing the results obtained tissue culture based assays for WNV infectivity, 100% of the mice infected with $10^4$ pfu of 20 μM MB-treated WNV were still alive at day 15 (FIG. 3, panel A, gray squares). It is contemplated that vaccines for other RNA viruses as described herein can be similarly used for inoculation. The difference in survival was significant to $p \leq 0.0015$ at day 15 using Student's t-test.

An active immune system within the BalbC/j mice could contribute to blocking infection in the MB treated group. It is possible that if only a few infectious particles survived the MB photo-inactivation then host immune response would impede the disease. To rule out this possibility, we repeated the experiment using severe-combined immune deficient (SCID) mice. Two groups of C.B. 17-SCID mice (n=5 per group) were infected i.p. with $10^4$ pfu of MB-treated or mock-treated virus. 60% of the mock-treated group succumbed to infection by day 8, and all mice in this group were dead by <9 days (FIG. 3, panel B, black dots). This yields a mean survival of less than 9 days, which was almost identical to that of the BalbC/j mice. Similar to the BalbC/j mice animals injected with MB-treated WNV survived to day 15 and beyond days (FIG. 3, panel B, gray squares). At day 15 p.i. we calculated $p \leq 0.0023$ by Student's t-test. This result rules out the possibility that host immunity played a role in stopping WNV disease in these mice and established the 20 μM MB can stop WNV-associated morbidity and mortality in vivo.

(d) Efficacy of WNV Vaccine in Mice

As shown in FIG. 4, we have established a mouse model for WNV using immune competent BALB/cJ and immunodificient C.B.17-SCID mice. Using i.p. injection of $10^4$ pfu WNV strain OK02, we found that 100% of BALB/cJ and 100% of C.B.17 SCID mice succumb to infection as measured by Kaplan-Meier plot (FIG. 4, panel A and B). The mice develop hind-leg paralysis and present with encephalitis at autopsy (data not shown). Regardless of the host immune status (naïve, SCID, immunized/2° infection) mice that succumb to WNV infection die between eight and nine days suggesting that in those animals the virus overwhelms the host response.

A single exposure of $10^4$ pfu of MB-inactivated WNV vaccine significantly protects against diseases and delays mortality upon subsequent challenge with $10^4$ pfu live virus (FIG. 4, panel C). As expected, exposure of immunodeficient SCID mice to chemically inactivated WNV (FIG. 4, panel D) did not protect from subsequent infection. This shows that MB-inactivated WNV vaccine acts by using the host adaptive (B cells and T cells) host immune system, which is not present in SCID mice.

Figure 6:
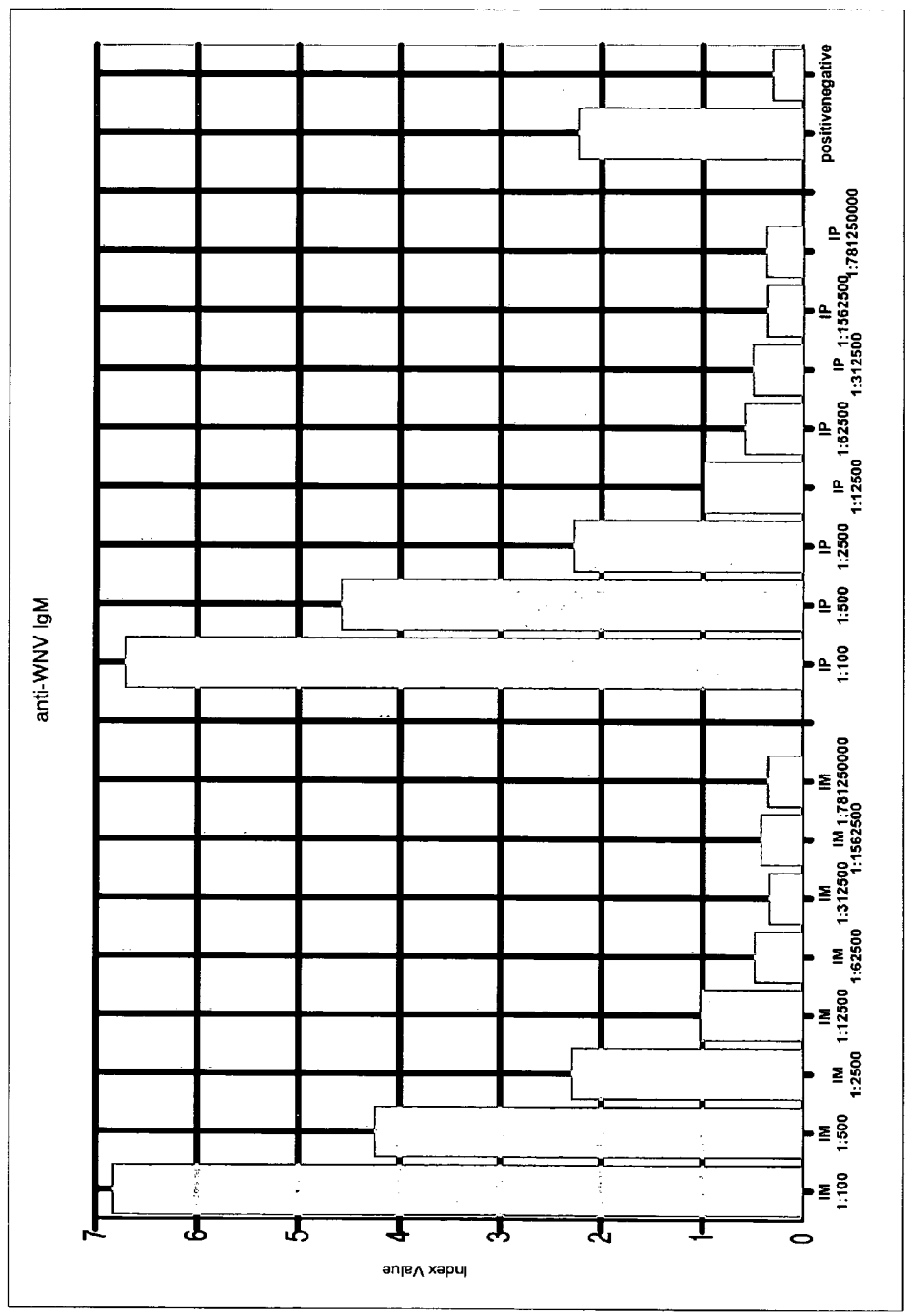
FIG. 6: Anti-WNV specific IgG antibody titers after immunization either intra muscular (IM) or intra peritoneal (IP) of mice with MB-inactivated WNV.
Figure 7:
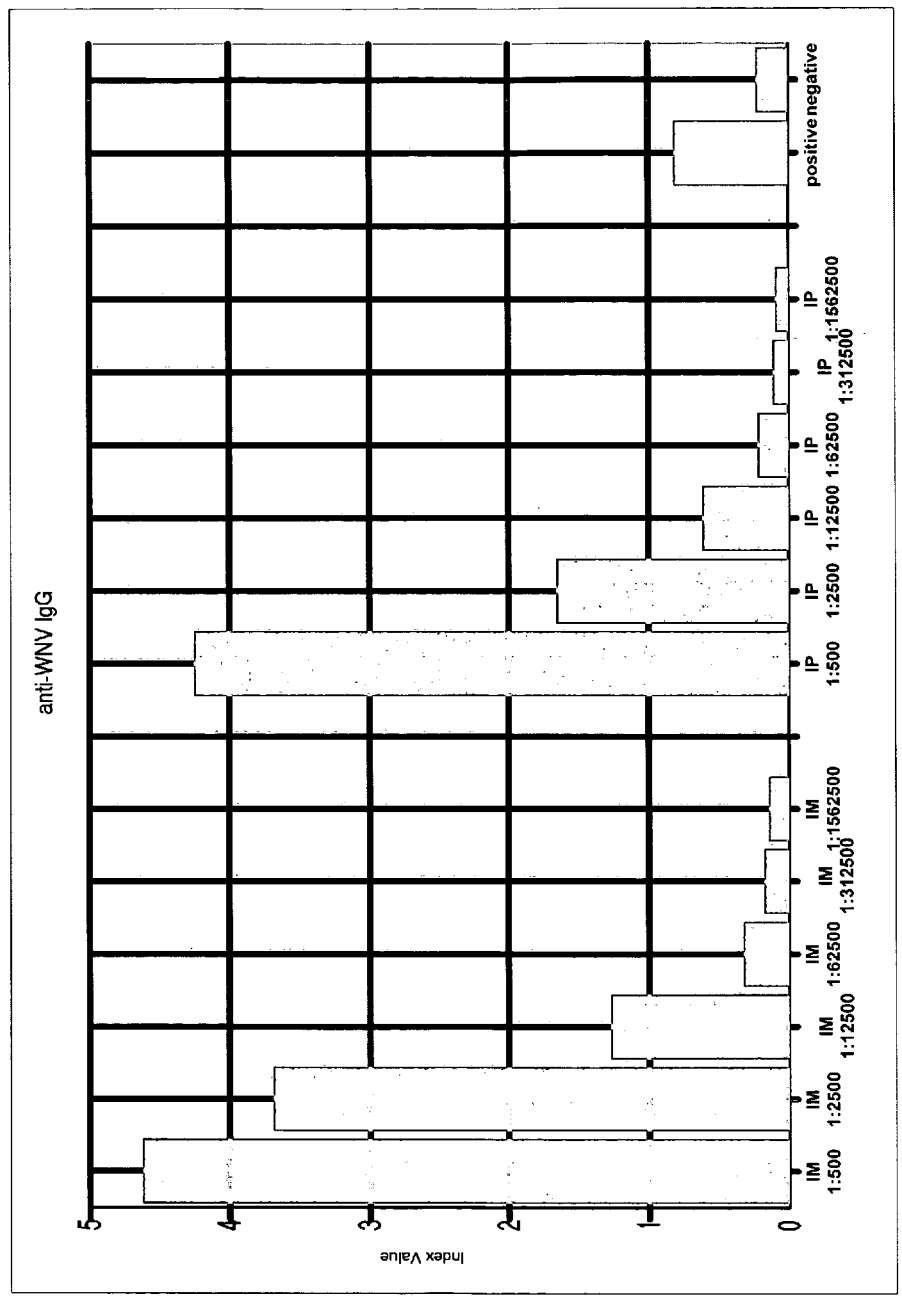
FIG. 7: Anti-WNV specific IgM antibody titers after intra muscular (IM) or intra peritoneal (IP) immunization of mice with MB-inactivated WNV.

In people, WNV infection causes high titer antibodies of type IgM and IgG. These neutralize and ultimately clear the virus leading to resolution of infection and disease. The present West-Nile virus vaccine induces high titer IgM and IgG antibodies (FIGS. 6 and 7, respectively). The induction of such antibodies by a vaccine is a major indicator of vaccine efficacy. Anti-WNV antibodies are considered for therapeutic use and proven to prevent WNV infection in mice (Gould, 2005; Oliphant, 2005). We pooled the sera from mice that were immunized with MB+WNV, challenged with WNV and survived (FIG. 8) and tested for the presence of anti WNV antibodies of type IgG and type IgM using the FDA-approved ELISA (FOCUS INC.). Pooled mouse sera were diluted in saline as indicated and tested (in duplicate) for reactivity according to the manufacturers recommendations. Also included were positive and negative controls. An index value of $\geq 1.0$ for IgM and $\geq 0.6$ for IgG was considered positive. This establishes end-point dilution titers of 1:12,500, which is comparable to titers obtained by other vaccine candidates (Ledizet, 2005). West-Nile virus vaccine protects mice against infection after inter muscular (i.m.) and inter peritoneal (i.p.) inoculation. We repeated our mouse vaccination experiment with a second set of mice using either intra muscular or intra peritoneal immunization of 103 pfu WNV & MB. As shown in FIG. 8, both routes of immunization protected mice from subsequent challenge (p $\leq 0.05$ by t-test).

(e) Real-Time Quantitative RT-PCR Across the WNV Genome

Figure 5:
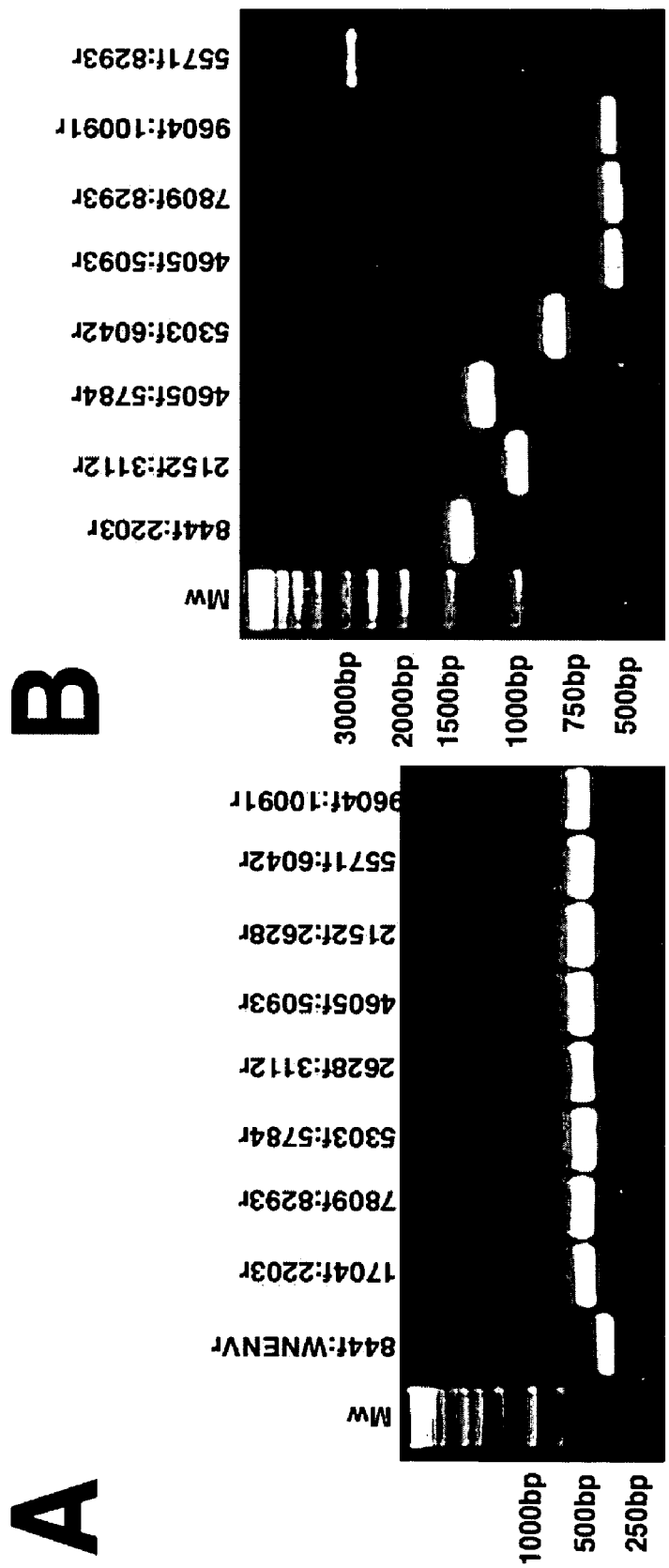
FIGS. 5 A and B shows Agarose gel images of amplification products from 18 WNV specific primers.

To expand upon this development we designed real-time quantitative RT-PCR primers that, in combination, span almost the entire WNV genome (FIG. 5). In contrast to prior published work, all of the primer pairs used herein (see Table 2, SEQ ID Nos. 1-18) work the same, at highly stringent annealing temperature of 60° C. and therefore can be utilized in a 96 well high-throughput format. We have adapted PCR conditions such that these primers will yield a product even when up to three nucleotide mismatches are present in the primer binding site.

TABLE 2

Oligonucleotide Primers Used in RT-PCR

| SEQ ID | Direction | Product Size (bp) | Genome Start Position* | Length | Tm | GC % | Sequence |
|---|---|---|---|---|---|---|---|
| 1 | Forward | 499 | 1724 | 20 | 59.02 | 50.00 | TAGCATTGGGCTCACAAGAG |
| 2 | Reverse | 499 | 2203 | 20 | 58.99 | 55.00 | GCTAGTCTCTGCGCTCCTTT |
| 3 | Forward | 504 | 7809 | 20 | 58.85 | 45.00 | CAGGAAAGAAGGCAATGTCA |
| 4 | Reverse | 504 | 8293 | 20 | 59.00 | 55.00 | AGTGGGTTTCTGACCAGTCC |
| 5 | Forward | 501 | 5303 | 20 | 58.70 | 50.00 | AGATGGCTGAAGCACTGAGA |
| 6 | Reverse | 501 | 5784 | 20 | 59.05 | 50.00 | ATTTTGGGTACTCCGTCTCG |
| 7 | Forward | 504 | 2628 | 20 | 58.91 | 55.00 | AGTGTGCGGTCTACGATCAG |

TABLE 2-continued

Oligonucleotide Primers Used in RT-PCR

| SEQ ID | Direction | Product Size (bp) | Genome Start Position* | Length | Tm | GC % | Sequence |
|---|---|---|---|---|---|---|---|
| 8 | Reverse | 504 | 3112 | 20 | 58.85 | 50.00 | TTGACTTCACCCAGAACTGC |
| 9 | Forward | 508 | 4605 | 20 | 58.94 | 50.00 | AAAGAGAGGAGGCGTGTTGT |
| 10 | Reverse | 508 | 5093 | 20 | 59.12 | 50.00 | CTGCACTATCGCGCTTATGT |
| 11 | Forward | 496 | 2152 | 20 | 59.29 | 50.00 | CATTGGCACAAGTCTGGAAG |
| 12 | Reverse | 496 | 2628 | 20 | 58.91 | 55.00 | CTGATCGTAGACCGCACACT |
| 13 | Forward | 491 | 5571 | 20 | 59.09 | 50.00 | AGGCACTTCAGATCCATTCC |
| 14 | Reverse | 491 | 6042 | 20 | 58.88 | 50.00 | AGTCGTCTTCATTCGTGTGC |
| 15 | Forward | 507 | 9604 | 20 | 58.94 | 45.00 | AAAGGGAAAGGACCCAAAGT |
| 16 | Reverse | 507 | 10091 | 20 | 58.75 | 55.00 | TGTCATCCACTCTCCTCCTG |
| 17 | Forward | 200 | 844 | 20 | 56.00 | 55.00 | TGGATCTTGAGGAACCCTGG |
| 18 | Reverse | 200 | 1209 | 21 | | | GGGTCAGCACGTTTGTCATTG |

* = Genome position according to WNV NY99 complete genome sequence (Lanciotti, et al., 1999).

These experiments demonstrate the efficacy of MB to photoinactivate WNV in tissue culture and, for the first time, demonstrate the absence of residual infectivity in an animal model of WNV infection. This result is consistent with prior work on MB (Mohr et al., 2004) and extends those studies in important ways including: (i) MB+light was able to inactivate multiple independent low-passage isolates of WNV from recent outbreaks 2002 and 2003; (ii) we determined the $IC_{50}$ to be 0.10 µM; when a concentration of 20 µM MB was used a reduction of $10^7$ pfu was achieved, which is higher than any WNV titer found in human blood products to date; (iii) MB+light-inactivated virus was no longer infectious in an animal model of WNV infection.

Laboratory mice are very sensitive to WNV infection (Beasley et al., 2002; Kramer and Bernard, 2001; Perelygin et al., 2002; Samuel, 2002). As little as 1 pfu/animal can be lethal and $10^3$ pfu causes mortality in 100% of infected animals within 7-8 days. MB+light treatment completely block-associated morbidity and mortality at challenge doses of $10^3$ and $10^4$ pfu per animal. MB has been used in the treatment of humans for many years. It is safe with the longest reported oral use for up to 19 months at 100 mg/kg (~50 µM in blood) twice daily with no reported side effects (Naylor et al., 1986). DiSanto and Wagner (1972) report that MB is absorbed orally and has a half-life of about 10 h. The in vivo half-life for MB+light-inactivated WNV still remains to be established, but our animal experiments imply that MB+light-inactivated WNV particles have no toxic side effects either. Use of this technology to inactivate a wide range of viruses in blood products will help to lessen the ever-increasing threat of viral infection from blood transfusion. It should also be noted that while blood is currently tested for infectious agents such as HIV-1, hepatitis C, and WNV; the blood units which test positive cannot be used. MB+light inactivtion technology could combat blood shortages by rendering these once useless blood samples useful again. This is particularly useful in developing nations or in a time of war.

Utility

The present invention in one embodiment is directed to vaccines against RNA viruses, in particular RNA viruses in the family Flaviviridae, which includes for example West Nile Virus, Yellow fever virus, Dengue fever virus, Hepatitis C virus, Pestiviruses, Bovine viral diarrhea virus, and Classical Swine fever virus (and others as described herein), the vaccine comprising an RNA virus or immunogenic portions thereof, which have been treated and rendered inactive by Methylene Blue (MB), or derivatives thereof, and visible light. Similarly the RNA virus or immunogenic portion thereof may have been inactivated by other phenothiazine dyes, including Methylene Green, 1-methyl MB, 1,9-dimethyl MB, Azure A, Azure B, Azure C, thionine, and toluidine blue, or by squalene. More broadly, the invention comprises a vaccine or composition comprising one or more RNA viruses which have been inactivated by chemicals which induce RNA:RNA or RNA:protein crosslinking.

Further, the invention contemplates vaccines produced via the above inactivation techniques which are directed against any RNA virus including, but not limited to influenza, HIV and NIAID category A and category B priority pathogenic viruses or any other RNA virus described herein.

The present invention also contemplates novel strains of WNV (OK02 and OK03) which can be used herein in to produce a vaccine.

The present invention also contemplates and describes herein novel primers and their use in recognizing and amplifying all of or portions of the WNV genome for diagnosing WNV infections or for identifying the presence of WNV in blood or blood products, or that can recognize and amplify the entire viral genome of the NIAID category A or B priority pathogens.

More particularly, the present invention provides a vaccine composition which comprises an effective immunizing amount of an immunogenically active component selected from the group consisting of one or more inactivated whole, subunits or portions, of a West Nile Virus (including, but not limited to, WNV strains NY-99, OK02 and OK03 or others indicated below), an antigen derived from said virus, and a mixture thereof; and a pharmacologically acceptable carrier wherein the whole virus, portion, or subunit or antigenic component thereof was provided by inactivating the one or more strains of West Nile Virus or components thereof by exposure to Methylene Blue (or other dyes or compounds described herein) and visible light. WNV strains that could be treated as described herein to produce an inactive immunogenic WNV vaccine include but are not limited to OK02, OK03, NY99, Cm-CT99, Crow-NJ99, Crow-NY99, C.pipiens-NY99, Eq.-NY99, HB709-NY99, HB743-NY99, US AMRIID99, and 2741.

The present invention also provides a method for the prevention or amelioration of a disease caused by a particular RNA virus in a human or animal subject which comprises administering to said subject an RNA virus vaccine composition as described above disposed in a pharmacologically acceptable carrier to induce an immunogenic response effective against the RNA virus in vivo.

As used herein, the term "immunogenic or immunogenically active" designates the ability to stimulate an immune response, i.e., to stimulate the production of antibodies, particularly humoral antibodies, or to stimulate a cell-mediated response. For example, the ability to stimulate the production of circulating or secretory antibodies or the production of a cell-mediated response in local mucosal regions, (e.g., intestinal mucosa), peripheral blood, cerebral spinal fluid or the like.

The effective immunizing amount of the immunogenic or immunogenically active component may vary and may be any amount sufficient to evoke an immune response and provide immunological protection against an RNA virus disease as contemplated herein. Amounts wherein a dosage unit preferably comprises at least about $1\times10^3$ to $1\times10^4$ $TCID_{50}$ (Tissue Culture Infective Dose) of inactivated (i.e., treated as described herein) whole or subunit virus cells or antigen derived therefrom or a mixture thereof, and preferably at least about $1\times10^5$ $TCID_{50}$, are suitable. Even more preferably, at least about $1\times10^6$ $TCID_{50}$, are suitable. Even more preferably, at least about $1\times10^7$ $TCID_{50}$ per dosage unit may be utilized. It is especially desirable that at least about $1\times10^8$ $TCID_{50}$ of inactivated whole or subunit RNA virus cells or antigen derived therefrom or a mixture thereof be used in the vaccine composition of the invention. In certain embodiments, as much as $1\times10^9$ $TCID_{50}$ or $1\times10^{10}$ $TCID_{50}$ and more may be utilized. A quantity in the range of about $1\times10^4$ $TCID_{50}$ to about $1\times10^8$ $TCID_{50}$ is preferably utilized.

At least one dosage unit per subject is contemplated herein as a vaccination regimen. In some embodiments, two or more dosage units may be especially useful. A dosage unit of vaccine composition may typically be about 0.1 to 10 milliliters, preferably about 0.5 to 5 milliliters, and even more preferably about 1 to 2 milliliters, with each dosage unit containing the heretofore described quantity of virus or virus component. The skilled artisan will quickly recognize that a particular quantity of vaccine composition per dosage unit, as well as the total number of dosage units per vaccination regimen, may be optimized, so long as an effective immunizing amount of the virus or a component thereof is ultimately delivered to the subject.

The RNA virus vaccine composition of the present invention may also contain one or more adjuvants or excipients. As used herein the term "adjuvant" refers to any component, which improves the body's response to a vaccine. The adjuvant will typically comprise about 0.1 to 50% vol/vol of the vaccine formulation of the invention, more preferably about 1 to 50% of the vaccine, and even more desirably about 1 to 20% thereof. Amounts of about 4 to 10% may be even more preferred. Adjuvants are well known in the art thus further detailed description thereof herein is not deemed necessary.

In addition, the adjuvant may include one or more wetting or dispersing agents in amounts of about 0.1 to 25%, more preferably about 1 to 10%, and even more preferably about 1 to 3% by volume of the adjuvant. Particularly preferred as wetting or dispersing agents are non-ionic surfactants. Useful non-ionic surfactants include polyoxyethylene/polyoxypropylene block copolymers, especially those marketed under the trademark PLURONIC® and available from BASF Corporation (Mt. Olive, N.J.). Other useful nonionic surfactants include polyoxyethylene esters such as polyoxyethylene sorbitan monooleate, available under the trademark TWEEN 80®. It may be desirable to include more than one, e.g., at least two, wetting or dispersing agents in the adjuvant as part of the vaccine composition of the invention.

Other components of the adjuvant may include such preservative compounds as formalin and thimerosal in amounts of up to about 1% vol/vol of the adjuvant.

Pharmacologically acceptable carriers suitable for use in the vaccine composition of the invention may be any conventional liquid carrier suitable for pharmaceutical compositions, preferably a balanced salt solution, physiological saline, or other water-based solution suitable for use in tissue culture media. Other available carriers well known to those of ordinary skill in the art may also be utilized.

Additional excipients available and known to those of ordinary skill in the art may also be included in the vaccine composition according to the various embodiments heretofore described. For example, pH modifiers may be utilized.

The components of the vaccine composition of the invention as heretofore described, including the carrier, may be combined together using techniques known to those of ordinary skill in the art.

In one embodiment of the invention the immunogenically active component of the invention may be incorporated into liposomes using known technology such as that described in Nature, 1974, 252, 252-254 or the Journal of Immunology, 1978, 120, 1109-13. In another embodiment of the invention, the immunogenically active component of the invention may be conjugated to suitable biological compounds such as polysaccharides, peptides, proteins, polymers or the like, or a combination thereof.

In a preferred embodiment of the invention, the novel vaccine composition contemplated herein may be formulated in a dosage unit form as heretofore described to facilitate administration and ensure uniformity of dosage. Formulation may be effected using available techniques, such as those applicable to preparations of emulsions.

The novel vaccine composition contemplated herein may be administered, for example, by one or more of parenterally, intramuscularly, subcutaneously, intraperitoneally, intradermally, orally, intranasally, arterially, intraocularly, rectally, intralymphnodally, or vaginally, preferably in effective amounts according to a schedule which may be determined by the time of anticipated potential exposure to a carrier of or infection by any of the RNA viruses described herein. In this way, the subject may have time to build immunity prior to the natural exposure. By way of non-limiting example, a typical treatment schedule or dosing regimen may include parenteral administration, preferably intramuscular injection of one dosage unit, at least about 2-8 weeks prior to potential exposure. At least two administrations may be preferred, for example one dosage unit at about 8 weeks and a second dosage unit at about 3-5 weeks prior to potential exposure of the treated subject. As heretofore set forth, a dosage unit will typically be within the range of about 0.1 to 10 milliliters of vaccine composition containing the previously described amounts of active and percentages of adjuvant and inactives set forth. A dosage unit within the range of about 0.5 to 5 milliliters is perhaps more preferred, with about 1 to 2 milliliter(s) being particularly preferred.

The subjects which may be treated with the RNA virus vaccine contemplated herein include, but are not limited to, mammals, including primates such as humans, chimpanzees, baboons, gorillas and orangutans, monkeys and lemurs; mustelids including minks; camelids, including camels, llamas, alpacas, and vicunas; feuds including lions, tigers and domestic cats; canids including dogs; bovids including cattle; equids including horses; ovids including sheep and goats; suids including pigs; cervids including deer, elk and moose; and birds including chickens, turkey, ostriches, ducks, geese, pigeons, and parrots.

The present invention is not to be limited in scope by the specific embodiments described herein, since such embodiments are intended as but single illustrations of one aspect of the invention and any functionally equivalent embodiments are within the scope of this invention. Indeed, various modifications of the methods of the invention in addition to those shown and described herein will become apparent to those skilled in the art form the foregoing description.

CITED REFERENCES

Each of the references, patents or publications cited herein is incorporated by reference in its entirety.

Beasley, D. W., Li, L., Suderman, M. T., Barrett, A. D., 2002. Mouse neuroinvasive phenotype of West Nile virus strains varies depending upon virus genotype. Virology 296, 17-23.

CDC, 1999. Outbreak of West Nile-like viral encephalitis-New York, 1999. MMWR Morbid., Mortal. Wkly. Rep. 48, 845-849.

CDC, 2002. West Nile Virus Activity-United States, Jul. 31-Aug. 7, 2002, and Louisianna, Jan. 1-Aug. 7, 2002. MMWR Morbid, Mortal. Wkly. Rep. 51, 681-683.

DiSanto, A. R., Wagner, J. G., 1972. Pharmacokinetics of highly ionized drugs. II. Methylene blue-absorption, metabolism, and excretion in man and dog after oral administration. J. Pharm. Sci. 61, 1086-1090.

Dittmer, D. P. 2003. Transcription profile of Kaposi's sarcoma-associated herpesvirus in primary Kaposi's sarcoma lesions as determined by real-time PCR arrays. Cancer Res 63:2010-5.

Enserink, M., 2002. West Nile's Surprisingly Swift Continental Sweep. Science 297, 1988-1989.

Fakhari, F. D., and D. P. Dittmer. 2002. Charting Latency Transcripts in Kaposi's Sarcoma-Associated Herpesvirus by Whole-Genome Real-Time Quantitative PCR. J Virol 76:6213-23 using RNAzol (Tel-Test, Inc., Friendswood, Tex.).

Gould L H, Sui J, Foellmer H, Oliphant T, Wang T, Ledizet M, Murakami A, Noonan K, Lambeth C, Kar K, Anderson J F, de Silva A M, Diamond M S, Koski R A, Marasco W A, Fikrig E., "Protective and therapeutic capacity of human single-chain Fv-Fc fusion proteins against West Nile virus." *J Virol.* 2005 December; 79(23):14606-13.

Kramer, L., Bernard, K., 2001. West Nile virus infection in birds and mammals. Ann. NY Acad. Sci. 951, 84-93.

Lambrecht, B., Mohr, H., Knuver-Hopf, J., Schmitt, H., 1991. Photoinactivation of viruses in human fresh plasma by phenothiazine dyes in combination with visible light. Vox. Sang. 60, 207-213.

Lanciotti, R. S., Roehrig, J. T., Deubel, V., Smith, J., Parker, M., Steele, K., et al., 1999. Origin of the West Nile virus responsible for an outbreak of encephalitis in the northeastern United States. Science 286, 2333-2337.

Malet, I., M. Belnard, H. Agut, and A. Cahour. 2003. From RNA to quasispecies: a DNA polymerase with proofreading activity is highly recommended for accurate assessment of viral diversity. J Virol Methods 109: 161-70.

Mohr, H., Knuver-Hopf, J., Gravemann, U., Redecker-Klein, A., Muller, T. H., 2004. West Nile virus in plasma is highly sensitive to methylene blue-light treatment. Transfusion 44, 886-890.

Naylor, G. J., Martin, B., Hopwood, S. E., Watson, Y., 1986. A two-year double-blind crossover trial of the prophylactic effect of methylene blue in manic-depressive psychosis. Biol. Psychiatry 21, 915-920.

Oliphant T, Engle M, Nybakken G E, Doane C, Johnson S, Huang L, Gorlatov S, Mehlhop E, Marri A, Chung K M, Ebel G D, Kramer L D, Fremont D H, Diamond M S., "Development of a humanized monoclonal antibody with therapeutic potential against West Nile virus." *Nat. Med.* 2005 May; 11(5):522-30.

Papin, J. F., Vahrson, W., Dittmer, D. P., 2004b. SYBR green-based real-time quantitative PCR assay for detection of West Nile Virus circumvents false-negative results due to strain variability. J. Clin. Microbiol. 42 (4), 1511-1518.

Perelygin, A. A., Scherbik, S. V., Zhulin, I. B., Stockman, B. M., Li, Y., Brinton, M. A., 2002. Positional cloning of the murine flavivirus resistance gene. Proc. Natl. Acad. Sci. U.S.A. 99, 9322-9327.

Samuel, C. E., 2002. Host genetic variability and West Nile virus susceptibility. Proc. Natl. Acad. Sci. U.S.A. 99. 11555-115577.

What is claimed is:

1. An immunogenic composition, comprising:
   an inactivated whole West Nile virus wherein the West Nile virus is at least one of a strain OK02 having ATCC Accession No. PTA-8079 and a strain OK03 having ATCC Accession No. PTA-8078; and
   a pharmaceutically acceptable carrier or excipient.

2. The immunogenic composition of claim 1 wherein the inactivated whole West Nile virus has been inactivated by exposure to a phenothiazine dye and visible light.

3. The immunogenic composition of claim 1 wherein the phenothiazine dye is Methylene Blue, Methylene Green, 1-methyl Methylene Blue, 1,9-dimethyl Methylene Blue, Azure A, Azure B, Azure C, thionine, toluidine blue, or squalene.

4. The immunogenic composition of claim 1 further comprising an adjuvant.

5. The immunogenic composition of claim 1 further comprising at least one additional strain of a West Nile virus or immunogenic portion thereof, or at least one additional species of an RNA virus or an immunogenic portion thereof.

6. The immunogenic composition of claim 1 which is formulated to be administered parenterally, intramuscularly, intraocularly, subcutaneously, intraperitoneally, arterially, intradermally, orally, intranasally, intralymphnodally, rectally, vaginally, or by a combination of these routes.

* * * * *

UNITED STATES PATENT AND TRADEMARK OFFICE
CERTIFICATE OF CORRECTION

PATENT NO. : 7,767,210 B2  Page 1 of 1
APPLICATION NO. : 11/639023
DATED : August 3, 2010
INVENTOR(S) : Dirk P. Dittmer et al.

It is certified that error appears in the above-identified patent and that said Letters Patent is hereby corrected as shown below:

In the Specification:

Column 7, line 6: Delete "lade" and replace with -- clade --.

Column 17, line 19: After "vicunas:" delete "feuds" and replace with -- felids --.

Signed and Sealed this

Thirtieth Day of November, 2010

David J. Kappos
*Director of the United States Patent and Trademark Office*

SEQUENCE LISTING

```
<160> NUMBER OF SEQ ID NOS: 18

<210> SEQ ID NO 1
<211> LENGTH: 20
<212> TYPE: DNA
<213> ORGANISM: West Nile virus
```

```
<400> SEQUENCE: 1
tagcattggg ctcacaagag                                              20

<210> SEQ ID NO 2
<211> LENGTH: 20
<212> TYPE: DNA
<213> ORGANISM: West Nile virus

<400> SEQUENCE: 2
gctagtctct gcgctccttt                                              20

<210> SEQ ID NO 3
<211> LENGTH: 20
<212> TYPE: DNA
<213> ORGANISM: West Nile virus

<400> SEQUENCE: 3
caggaaagaa ggcaatgtca                                              20

<210> SEQ ID NO 4
<211> LENGTH: 20
<212> TYPE: DNA
<213> ORGANISM: West Nile virus

<400> SEQUENCE: 4
agtgggtttc tgaccagtcc                                              20

<210> SEQ ID NO 5
<211> LENGTH: 20
<212> TYPE: DNA
<213> ORGANISM: West Nile virus

<400> SEQUENCE: 5
agatggctga agcactgaga                                              20

<210> SEQ ID NO 6
<211> LENGTH: 20
<212> TYPE: DNA
<213> ORGANISM: West Nile virus

<400> SEQUENCE: 6
attttgggta ctccgtctcg                                              20

<210> SEQ ID NO 7
<211> LENGTH: 20
<212> TYPE: DNA
<213> ORGANISM: West Nile virus

<400> SEQUENCE: 7
agtgtgcggt ctacgatcag                                              20

<210> SEQ ID NO 8
<211> LENGTH: 20
<212> TYPE: DNA
<213> ORGANISM: West Nile virus

<400> SEQUENCE: 8
ttgacttcac ccagaactgc                                              20

<210> SEQ ID NO 9
<211> LENGTH: 20
<212> TYPE: DNA
<213> ORGANISM: West Nile virus
```

-continued

```
<400> SEQUENCE: 9
aaagagagga ggcgtgttgt                                              20

<210> SEQ ID NO 10
<211> LENGTH: 20
<212> TYPE: DNA
<213> ORGANISM: West Nile virus

<400> SEQUENCE: 10
ctgcactatc gcgcttatgt                                              20

<210> SEQ ID NO 11
<211> LENGTH: 20
<212> TYPE: DNA
<213> ORGANISM: West Nile virus

<400> SEQUENCE: 11
cattggcaca agtctggaag                                              20

<210> SEQ ID NO 12
<211> LENGTH: 20
<212> TYPE: DNA
<213> ORGANISM: West Nile virus

<400> SEQUENCE: 12
ctgatcgtag accgcacact                                              20

<210> SEQ ID NO 13
<211> LENGTH: 20
<212> TYPE: DNA
<213> ORGANISM: West Nile virus

<400> SEQUENCE: 13
aggcacttca gatccattcc                                              20

<210> SEQ ID NO 14
<211> LENGTH: 20
<212> TYPE: DNA
<213> ORGANISM: West Nile virus

<400> SEQUENCE: 14
agtcgtcttc attcgtgtgc                                              20

<210> SEQ ID NO 15
<211> LENGTH: 20
<212> TYPE: DNA
<213> ORGANISM: West Nile virus

<400> SEQUENCE: 15
aaagggaaag gacccaaagt                                              20

<210> SEQ ID NO 16
<211> LENGTH: 20
<212> TYPE: DNA
<213> ORGANISM: West Nile virus

<400> SEQUENCE: 16
tgtcatccac tctcctcctg                                              20

<210> SEQ ID NO 17
<211> LENGTH: 20
<212> TYPE: DNA
```

-continued

```
<213> ORGANISM: West Nile virus

<400> SEQUENCE: 17
tggatcttga ggaaccctgg                                               20

<210> SEQ ID NO 18
<211> LENGTH: 21
<212> TYPE: DNA
<213> ORGANISM: West Nile virus

<400> SEQUENCE: 18
gggtcagcac gtttgtcatt g                                             21
```